(12) United States Patent
Kearns et al.

(10) Patent No.: US 10,639,451 B2
(45) Date of Patent: May 5, 2020

(54) APPLICATORS FOR GRIPPING URINARY CATHETERS AND CATHETER ASSEMBLIES INCLUDING THE SAME

(71) Applicant: Hollister Incorporated, Libertyville, IL (US)

(72) Inventors: Barbara J. Kearns, Balla (IE); Martin P. Creaven, Ballina (IE); David A. Knauz, Riverwoods, IL (US); Daniel A. March, Lake Villa, IL (US)

(73) Assignee: Hollister Incorporated, Inc., Libertyville, IL (US)

( * ) Notice: Subject to any disclaimer, the term of this patent is extended or adjusted under 35 U.S.C. 154(b) by 0 days.

(21) Appl. No.: 15/758,987

(22) PCT Filed: Jun. 20, 2016

(86) PCT No.: PCT/US2016/052638
§ 371 (c)(1),
(2) Date: Mar. 9, 2018

(87) PCT Pub. No.: WO2017/053279
PCT Pub. Date: Mar. 30, 2017

(65) Prior Publication Data
US 2018/0280659 A1     Oct. 4, 2018

Related U.S. Application Data

(60) Provisional application No. 62/232,973, filed on Sep. 25, 2015.

(51) Int. Cl.
*A61M 25/01* (2006.01)
*A61M 25/00* (2006.01)

(52) U.S. Cl.
CPC .......... *A61M 25/01* (2013.01); *A61M 25/002* (2013.01); *A61M 25/0111* (2013.01); *A61M 25/0113* (2013.01); *A61M 2205/0216* (2013.01); *A61M 2210/1096* (2013.01)

(58) Field of Classification Search
CPC .... A61M 25/00; A61M 25/002; A61M 25/01; A61M 25/0111; A61M 25/0113; A61M 2205/0216; A61M 2210/1096
USPC ......................................................... 206/364
See application file for complete search history.

(56) References Cited

U.S. PATENT DOCUMENTS

| | | |
|---|---|---|
| 3,154,080 A | 10/1964 | Rowan et al. |
| 3,421,509 A | 1/1969 | Fiore |
| 4,051,849 A | 10/1977 | Poncy et al. |
| 4,834,711 A | 5/1989 | Greenfield et al. |
| 4,871,358 A | 10/1989 | Gold |

(Continued)

FOREIGN PATENT DOCUMENTS

| | | |
|---|---|---|
| DE | 19826746 C1 | 11/1999 |
| EP | 0972536 A1 | 1/2000 |

(Continued)

*Primary Examiner* — Bryon P Gehman
(74) *Attorney, Agent, or Firm* — Cook Alex Ltd.

(57) ABSTRACT

An applicator for gripping a urinary catheter. The applicator includes a body having a proximal end, a distal end and a lumen extending therethrough for receiving a catheter. The body includes at least one projection disposed within the lumen which contacts the catheter shaft to resist movement of the body along the catheter shaft.

15 Claims, 4 Drawing Sheets

(56) References Cited

U.S. PATENT DOCUMENTS

| | | | |
|---|---|---|---|
| 4,927,415 A * | 5/1990 | Brodsky | A61M 25/0625 604/192 |
| 5,242,428 A | 9/1993 | Palestrant | |
| 5,334,166 A | 8/1994 | Palestrant | |
| 5,368,575 A | 11/1994 | Chang | |
| 5,792,114 A | 8/1998 | Fiore | |
| 5,871,475 A | 2/1999 | Frassica | |
| 6,090,075 A | 7/2000 | House | |
| 6,355,004 B1 | 3/2002 | Pedersen et al. | |
| 6,402,726 B1 | 6/2002 | Genese | |
| 6,578,709 B1 | 6/2003 | Kavanagh et al. | |
| 6,602,244 B2 | 8/2003 | Kavanagh et al. | |
| 6,613,014 B1 | 11/2003 | Chi | |
| 6,676,651 B2 | 1/2004 | Haacke et al. | |
| 7,094,220 B2 | 8/2006 | Tanghoj et al. | |
| 7,601,158 B2 | 10/2009 | House | |
| 7,632,256 B2 | 12/2009 | Mosler et al. | |
| 7,938,807 B2 | 5/2011 | House | |
| 7,963,908 B2 | 6/2011 | Lindberg | |
| 8,181,778 B1 | 5/2012 | van Groningen et al. | |
| 8,328,792 B2 | 12/2012 | Nishtala et al. | |
| 8,523,823 B2 | 9/2013 | Ostfeld et al. | |
| 10,207,076 B2 * | 2/2019 | Foley | A61M 25/002 |
| 10,238,832 B2 * | 3/2019 | Gustavsson | A61M 25/002 |
| 10,406,322 B2 * | 9/2019 | O'Flynn | A61M 25/0111 |
| 2003/0018322 A1 | 1/2003 | Tanghoj et al. | |
| 2003/0060807 A1 | 3/2003 | Tanghoj et al. | |
| 2005/0096688 A1 | 5/2005 | Slazas et al. | |
| 2007/0088330 A1 | 4/2007 | House | |
| 2008/0015527 A1 | 1/2008 | House | |
| 2008/0051630 A1 | 2/2008 | Levey et al. | |
| 2008/0171973 A1 | 7/2008 | House | |
| 2009/0043287 A1 | 2/2009 | Mosler et al. | |
| 2009/0099532 A1 | 4/2009 | Cuevas et al. | |
| 2010/0030197 A1 | 2/2010 | House | |
| 2010/0258568 A1 | 10/2010 | Frederiksen et al. | |
| 2010/0286664 A1 | 11/2010 | Haslinger | |
| 2011/0060317 A1 | 3/2011 | Frojd | |
| 2012/0168324 A1 | 7/2012 | Carleo | |
| 2012/0239005 A1 | 9/2012 | Conway et al. | |
| 2013/0144271 A1 | 6/2013 | Passadore et al. | |
| 2013/0231641 A1 | 9/2013 | Gustaysson | |
| 2014/0066904 A1 | 3/2014 | Young | |
| 2014/0066905 A1 | 3/2014 | Young | |
| 2014/0276661 A1 * | 9/2014 | Hannon | A61M 25/002 604/544 |
| 2014/0257250 A1 | 11/2014 | Palmer | |
| 2017/0056622 A1 * | 3/2017 | O'Flynn | A61M 25/0111 |
| 2018/0104444 A1 * | 4/2018 | Yin | A61M 25/002 |

FOREIGN PATENT DOCUMENTS

| | | |
|---|---|---|
| EP | 1485158 B1 | 1/2008 |
| EP | 2016821 A1 | 1/2009 |
| EP | 2105158 A2 | 9/2009 |
| EP | 2106821 A1 | 10/2009 |
| EP | 2471569 A1 | 7/2012 |
| EP | 2636421 A1 | 9/2013 |
| GB | 322426 | 12/1929 |
| SE | 518002 C2 | 8/2002 |
| WO | WO 00/30575 A1 | 6/2000 |
| WO | WO 01/74417 A2 | 10/2001 |
| WO | WO 03/002178 A2 | 1/2003 |
| WO | WO 03/008029 A2 | 1/2003 |
| WO | WO 2006/121508 A2 | 11/2006 |
| WO | WO 2007/106431 A2 | 9/2007 |
| WO | WO 2010/129362 A1 | 11/2010 |
| WO | WO 2011/011023 A1 | 1/2011 |
| WO | WO 2011/019359 A1 | 2/2011 |
| WO | WO 2012/176189 A1 | 12/2012 |

\* cited by examiner

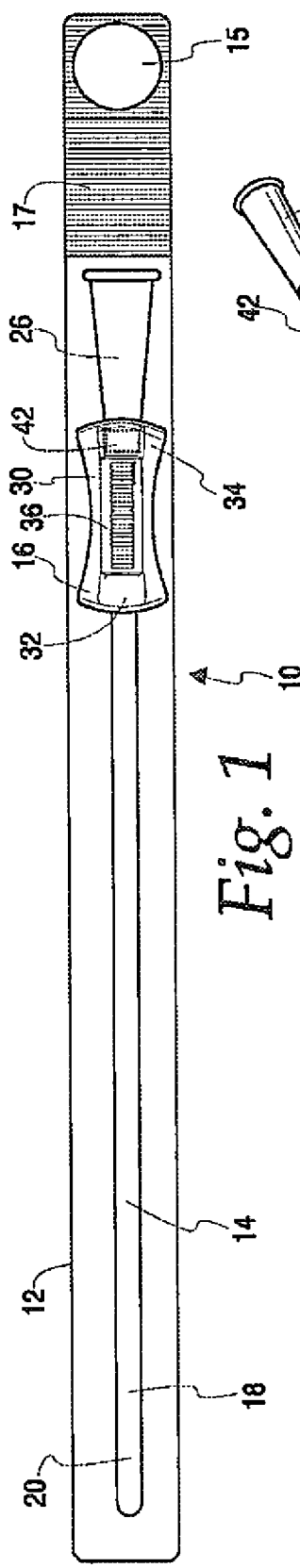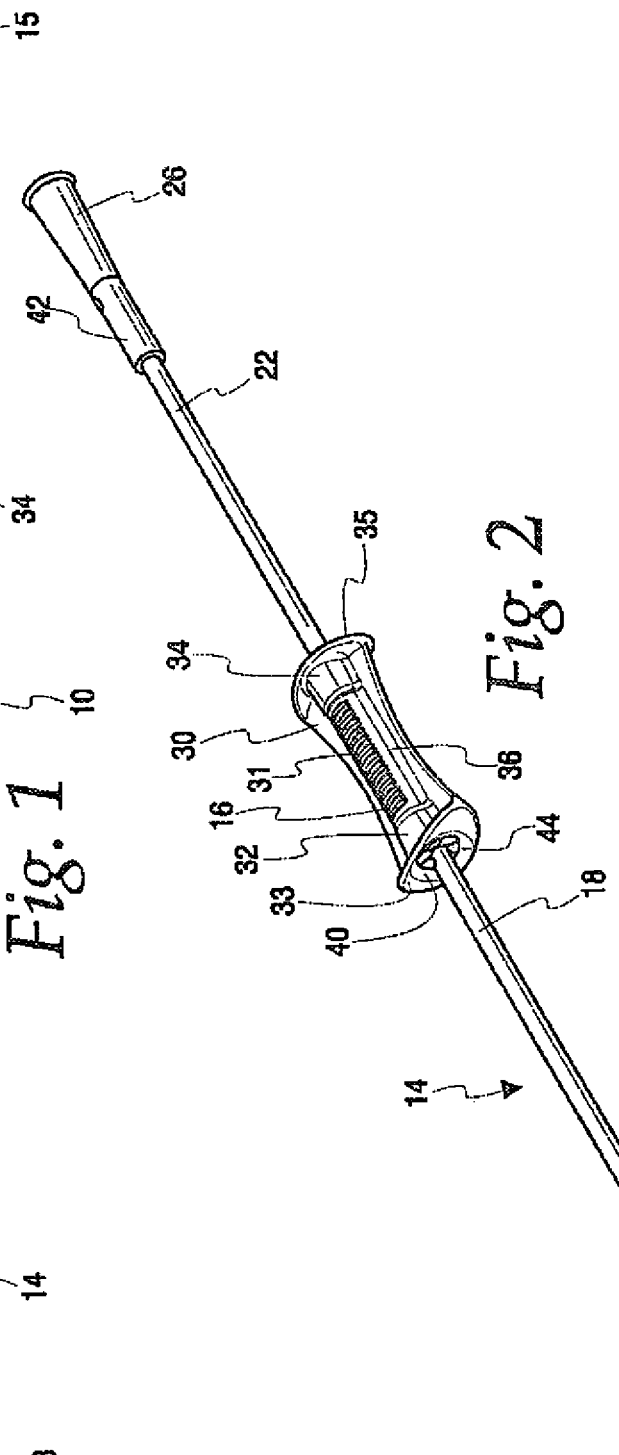

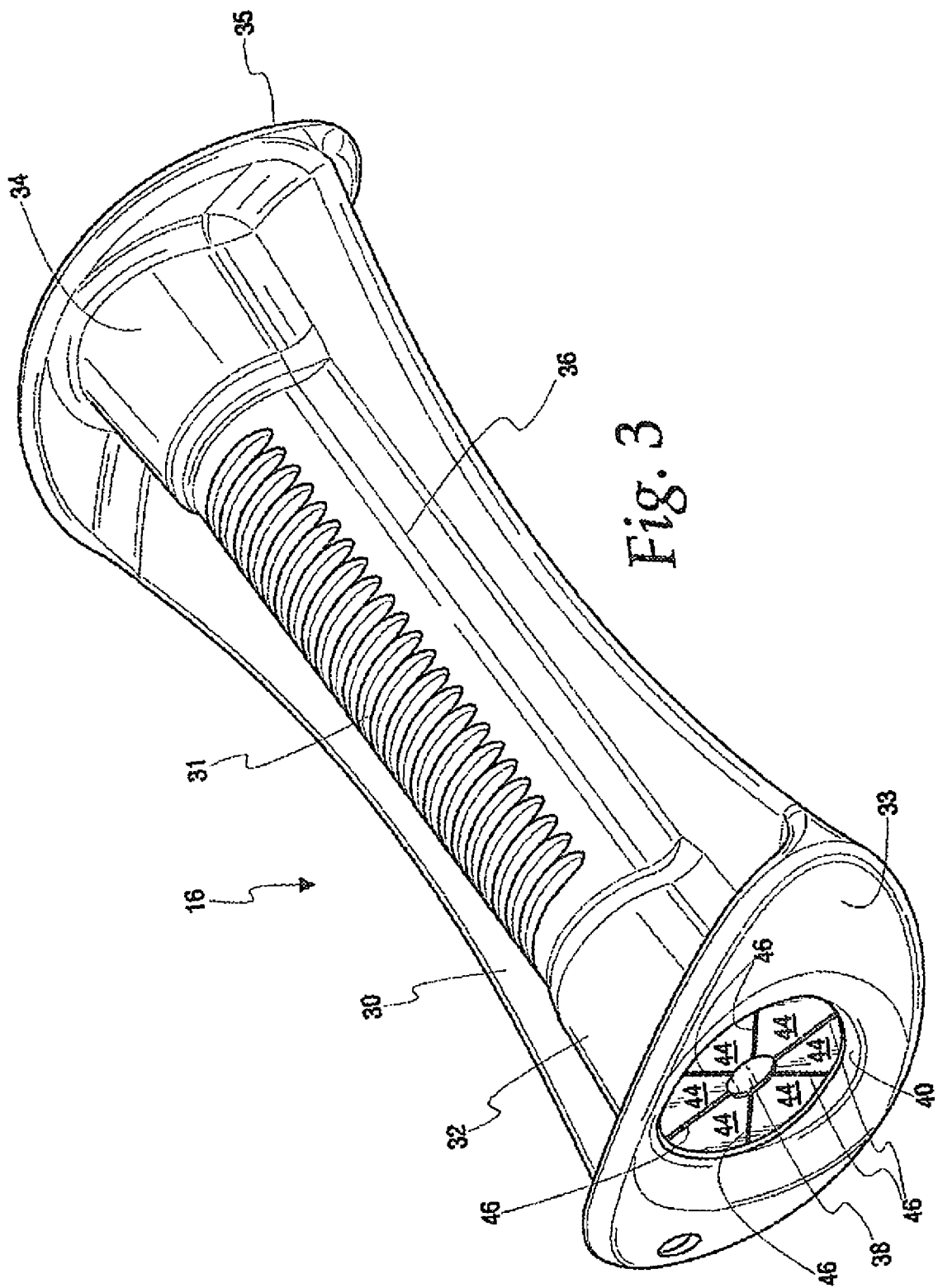

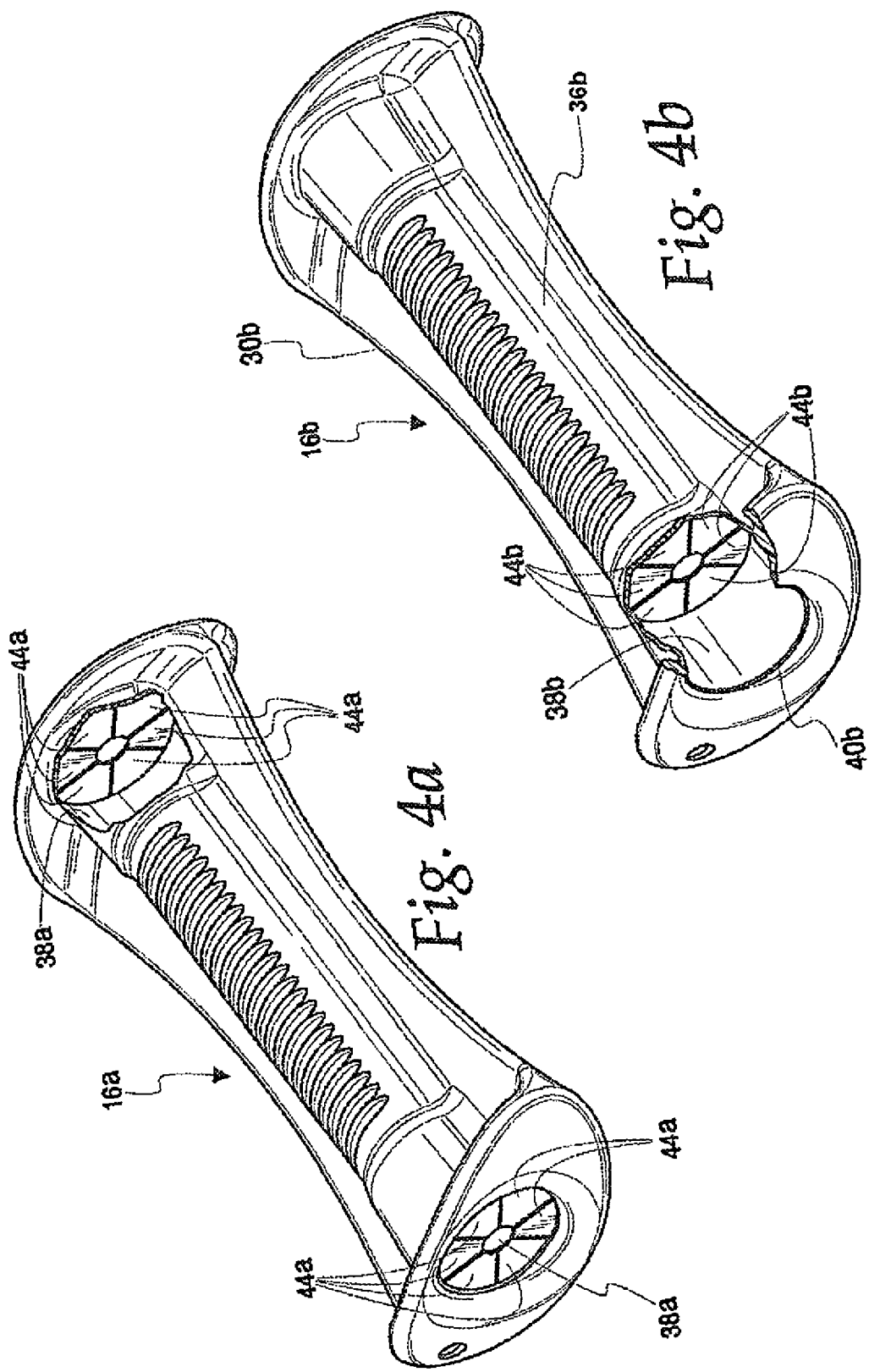

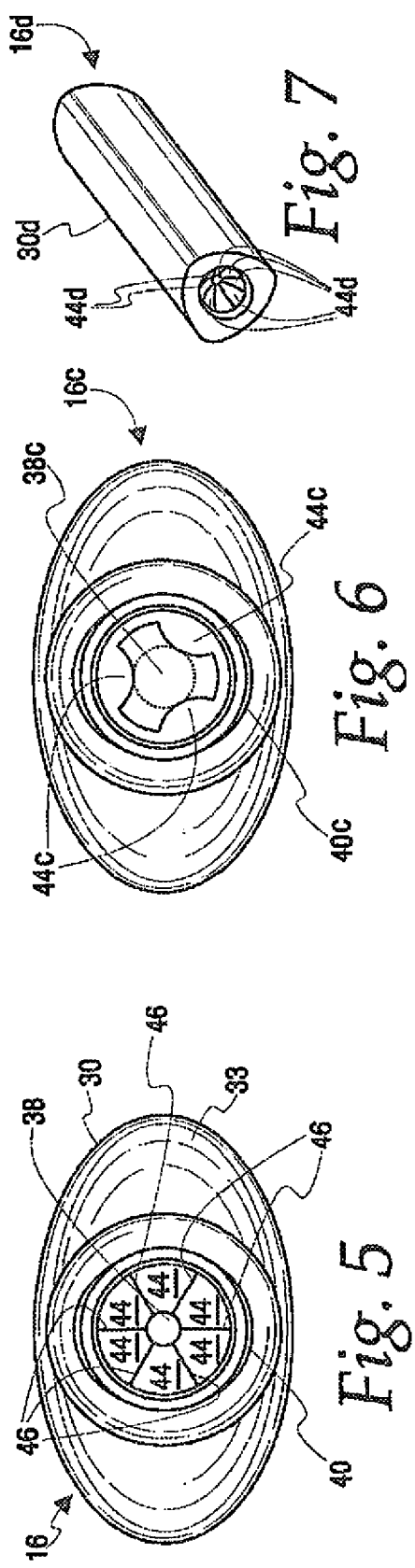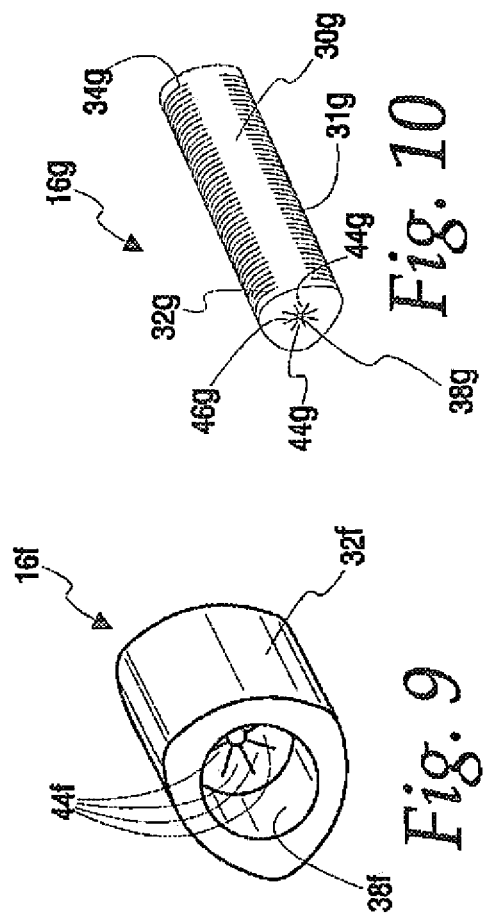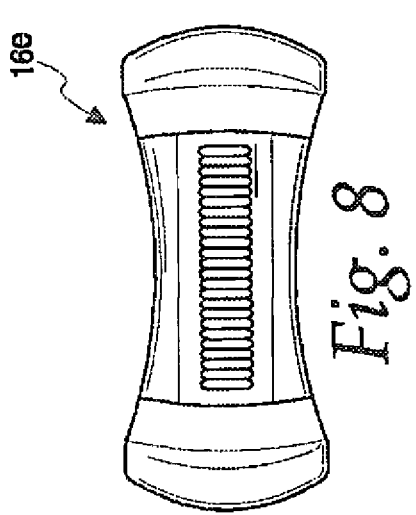

APPLICATORS FOR GRIPPING URINARY CATHETERS AND CATHETER ASSEMBLIES INCLUDING THE SAME

This is a U.S. National Stage of PCT International Patent Application No. PCT/US2016/052638, filed Sep. 20, 2016, which claims the priority and benefit to U.S. Provisional Patent Application Ser. No. 62/232,973, filed Sep. 25, 2015, both of which are hereby incorporated herein by reference.

DESCRIPTION

Technical Field

The present disclosure generally relates to the handling of intermittent urinary catheters during use, and more particularly, to applicators for gripping and handling catheters during use, and intermittent urinary catheter assemblies having such applicators associated with the catheters.

BACKGROUND

Intermittent catheterization is a good option for many users who suffer from various abnormalities and pathologies of the urinary system and the nerves associated therewith. Such catheters are typically provided as single use, individually packaged items and may include a gel-lubricant or hydrophilic coating as a lubricant for reducing friction during insertion into the urethra.

In many cases, intermittent catheterization is performed by self-catheterization wherein the user inserts the catheter into and through his/her urethra until the proximal end portion of the catheter reaches the bladder. The bladder is then drained through the catheter. Preferably, the catheters are designed for easy and contamination free handling.

One concern with the use of intermittent catheters is contamination and resulting infections that may occur from handling the catheter prior to insertion and use. Contamination of the insertable portion of the catheter can lead to urinary tract infections. One source of contamination is the user directly touching the insertable portion of the catheter while removing the catheter from the package and inserting it into the urethra. To that end, it is preferable that the catheter be handled and inserted without the user directly touching the insertable portion of the catheter.

Thus, there is a need for catheter assemblies which may be handled and inserted without directly touching the insertable portion of the catheter.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, an applicator for gripping a urinary catheter includes a body having a proximal end and a distal end and a lumen extending therethrough. The lumen has a proximal end opening and a distal end opening and is configured to receive a shaft of a urinary catheter therethrough so that the body is movable distally and proximally along the catheter. The applicator also includes at least one projection disposed within the lumen such that when the catheter shaft is received through the lumen, the at least one projection contacts the catheter shaft to resist movement of the body along the catheter shaft.

In another aspect, a urinary catheter assembly includes a catheter package having a cavity and a urinary catheter disposed within the cavity. The catheter includes a catheter shaft having a proximal insertion end portion and a distal end portion and a drainage member associated with the distal end portion of the catheter shaft. The assembly also includes an applicator for gripping the catheter located within the cavity. The applicator includes a body having a proximal end and a distal end and a lumen extending through the proximal and distal ends of the body. The lumen has a proximal end opening and a distal end opening and the shaft of the catheter is located within and extends through the lumen. The body is positioned distal of the proximal insertion end portion of the catheter and is movable proximally and distally along the catheter. The applicator also includes at least one projection disposed within the lumen and in contact with the catheter shaft to resist movement of the body along the catheter shaft.

BRIEF DESCRIPTION OF THE DRAWINGS

FIG. 1 is a top plan view of an intermittent catheter assembly of the present disclosure including a catheter package, intermittent urinary catheter and an applicator for gripping the catheter;

FIG. 2 is a perspective view of the intermittent urinary catheter of FIG. 1, showing the applicator moved proximally along the catheter shaft;

FIG. 3 is an enlarged perspective view the applicator shown in FIG. 1;

FIG. 4a is a perspective view of an alternative embodiment of an applicator in accordance with the present disclosure;

FIG. 4b is a perspective view of another alternative embodiment of an applicator in accordance with the present disclosure;

FIG. 5 is an end elevational view of the applicator of FIG. 3;

FIG. 6 is an end elevational view of an alternative embodiment of an applicator in accordance with the present disclosure;

FIG. 7 is a perspective view of an alternative embodiment of an applicator in accordance with the present disclosure;

FIG. 8 is a top view of an alternative embodiment of an applicator in accordance with the present disclosure;

FIG. 9 is a perspective view of an alternative embodiment of an applicator in accordance with the present disclosure; and FIG. 10 is a perspective view of an alternative embodiment of an applicator in accordance with the present disclosure.

DETAILED DESCRIPTION OF THE ILLUSTRATED EMBODIMENTS

The embodiments disclosed herein are for the purpose of providing a description of the present subject matter, and it is understood that the subject matter may be embodied in various other forms and combinations not shown in detail. Therefore, specific embodiments and features disclosed herein are not to be interpreted as limiting the subject matter as defined in the accompanying claims.

FIG. 1 shows an intermittent catheter assembly 10 according to an aspect of the present disclosure. The catheter assembly 10 includes a catheter package 12, a catheter 14 and an applicator 16. In the illustrated embodiment, the catheter package 12 defines a sealed cavity in which the catheter 14 and applicator 16 are disposed. The package 12 may be formed from front and back sheets of material that are attached to each about the periphery of the sheets. The sheets may be, for example, laminate sheets that include polymer and/or metal layers. In other embodiments, package 12 may be formed of a single sheet wherein the package is formed by flow-wrapping. In still other embodiments the package may be any suitable catheter package. Additionally, the package may include a ring shaped opening 15 at one or both ends thereof for handling and opening package 12. In the illustrated embodiment, ring shaped opening 15 is located in end seal region 17.

Referring to FIGS. 2 and 3, the illustrated intermittent catheter 14 includes a generally flexible catheter shaft 18, which extends between a closed proximal end portion 20 and an open distal end portion 22. The catheter shaft 18 may be provided generally according to conventional design, such as with one or more openings or eyes 24 associated with the proximal end portion 20 for flowing a fluid from the outside environment into the hollow interior of the catheter shaft 18. The distal end portion 22 is illustrated with an associated drainage member, such as a funnel 26, which may be a generally rigid component that is secured to the distal end portion 22 of the catheter shaft 18. The drainage funnel 26 may be configured to direct fluid from out of the interior of the catheter shaft 18 to a collection container or disposal device, such as a toilet. The catheter shaft 18 may be provided as a hydrophilic catheter shaft, in which case it may include a hydrophilic outer surface along at least a portion of its length. If provided, the hydrophilic portion of the catheter shaft becomes lubricious when wetted or hydrated with a hydration fluid, such as liquid water or saline or water vapor. All or a portion of the catheter shaft 18 itself may have hydrophilic properties or, alternatively, a coating may be applied to at least a portion of the outer surface of the catheter shaft 18 to give the coated portion hydrophilic properties. In other embodiments, the catheter may be lubricated with a gel-lubricant, which may be supplied with the catheter assembly or supplied separately.

The applicator 16 is a gripping or handling member that may be grasped by the user to grip and handle the catheter 14 during removal of catheter 14 from the catheter package 12 and insertion of catheter 14 into the urethra. Referring to FIGS. 1-3, the applicator 16 includes a body 30 having a proximal end portion 32, a distal end portion 34, and an intermediate portion 36. Body 30 may have a length between about 3.5 cm and 5 cm and in one embodiment may between about 4 cm and about 4.5 cm. In another embodiment, the length of the body may be between about 4.3 cm and 4.4 cm. The Body 30 additionally may be greater or smaller than 3.5 cm to 5 cm. A lumen or bore 38 extends through the proximal and distal end portions 32, 34 of body 30. The lumen 38 includes a proximal end opening 40 and a distal end opening (not shown). Referring to FIGS. 1 and 2, catheter shaft 18 is received into and passes through the lumen 38 so that applicator 16 is mounted on the catheter.

At least a portion of the body may be made from a flexible elastic material, such as an elastic polymeric material. In the illustrated embodiment, optionally, at least the intermediate portion 36 of body 30 is made of a deformable, flexible elastic material which may be deformed, bent or compressed when grasped and squeezed by the user to grasp and handle the catheter and substantially returns to its original shape when the grasp is released or loosened. The intermediated portion 36 may optionally include an outer textured surface, such as ribbed surface 31, that assists the user in grasping the applicator 16. Oftentimes, users insert the catheter by feel and without visually monitoring the insertion. In this case, the textured surface may not only enhance the user's grasp of the applicator 16, but also may provide a tactile indication that the user has grasped the applicator 16 at the desired location. Furthermore, the proximal and distal faces 33, 35 of applicator 16 may be larger and/or may have a periphery that is larger than the intermediate portion 36. These larger faces 33, 35 also provide tactile guidance which may guide the user's fingers to the intermediate portion 36. The larger faces 33, 35 may also act as a stop during use. For example, the faces 33, 35 may act as a stop that abuts the glans penis in male users or the clitoral glans in female users.

As shown in FIG. 1, when in the package, applicator 16 may be mounted on catheter shaft 18 and be initially located at a position that is distal of proximal insertion end 20 of shaft 18. In the embodiment shown, applicator 16 is initially positioned at distal end 22 of catheter shaft 18. Optionally, applicator 16 may be releasably attached to drainage funnel 26. For example, the distal opening of applicator 16 may be dimensioned to receive the proximal end portion 42 of the funnel 26 and form a friction fit therewith. In one embodiment, the distal opening may be larger than the intermediate portion of the lumen 38 or the remaining portion of the lumen 38 to accommodate the proximal end portion 42 of the funnel 26. The applicator 16 may be separated from the drainage funnel 42 by the user moving the applicator 16 proximally along catheter shaft 18.

Referring to FIGS. 2, 3 and 5, body 30 of applicator 16 may include at least one projection 44, or other internal mechanism, that extends radially inwardly into lumen 38. When catheter shaft 18 is inserted into lumen 38, projection(s) 44 contacts the catheter shaft 18 to resist movement of applicator 16 along catheter shaft 18 when applicator 16 is at rest (i.e. not intentionally being moved by the user). The projection(s) 44 substantially limit free movement of applicator 16 until the user affects movement of the applicator. This allows applicator 16 to be selectively moveable along the catheter shaft by the user in that applicator 16 remains stationary relative to the catheter shaft until the user affects movement of the applicator along the shaft. In one embodiment, projection(s) 44 may remain in constant contact with the catheter extending through the lumen, even when applicator 16 is at rest and the user is not grasping or affecting movement of the applicator. Such resistance assists in maintaining applicator 16 mounted on catheter shaft 18 during removal of catheter 14 from package 12 and insertion of catheter shaft 18 into the urethra so that applicator 16 does not unintentionally move proximally along catheter shaft 18 and fall off the catheter shaft during use. For example, if the user were to remove catheter 14 from package 12 by grasping the funnel and holding catheter 14 in a vertical orientation, the contact between projection(s) 44 of applicator 16 and shaft 18 will prevent applicator 16 from unintentionally moving along catheter shaft 18 and/or falling off shaft 18.

In the embodiment illustrated in FIGS. 2, 3 and 5, projection(s) 44 are flexible petals or flaps that are separated or defined by slits or openings 46 located between adjacent petals. When catheter shaft 18 is located within lumen 38 of applicator 16, the petals contact catheter shaft 18 thereby providing resistance of relative movement between shaft 18 and applicator 16. The projections/petals 44 are sufficiently rigid to provide resistance to relative movement between applicator 16 and shaft 18 when no force is applied to the applicator 16 and/or shaft 18, and sufficiently flexible to allow applicator 16 to be moved relative to shaft 18 when force is applied by the user.

In the embodiment shown, the projection(s) 44 are located in or adjacent to proximal end opening 40 of lumen 38 of applicator 16. In other embodiments, the projection(s) may be located at other and/or additional locations. For example, in the embodiment shown in FIG. 4a, the applicator 16a has similar features to that of applicator 16, except that applicator 16a includes projections 44a located in both the proximal end opening 40a and the distal end opening 41a. In particular, applicator 16 includes a first set of projections 44a located in the proximal opening of lumen 38a and a second set of projections 44a located in the distal opening 41a. In the embodiment shown in FIG. 4b, applicator 16b also has similar features to that of applicator 16, except that the projections 44b are located distal of proximal end opening 40b of lumen 38b and proximal of the distal end opening. In one embodiment, projections 44b are located in intermediate portion 36b of body 30b of applicator 16b.

FIGS. 6-10 illustrate alternative embodiments and additional features that may be used with the applicators disclosed herein. Referring to FIG. 6, applicator 16c includes the plurality of rounded projections 44c that extend radially inwardly into the lumen 38c. In the illustrated embodiment, projections 44c include three uniformly spaced apart projections. In other embodiments, there may be more or less than three projections and/or such projections may or may not be uniformly spaced apart. Projections 44c are shown located in opening 40a. However, projections 44c may be located at any location along lumen 38c.

FIG. 7 illustrates a generally elongated applicator 16d, which has a generally uniformed shaped cross-section. In the illustrated embodiment, applicator 16d has a body 30d having a generally triangular cross-section. In other embodiments, the cross-section of applicator 16d may be other regular or irregular shapes, such as circular, oval or rectangular. The applicator includes projections 44d that extend radially inwardly into lumen 38d at a rearward angle. The projection 44d may also extend at a forward angle.

In FIG. 8, the applicator 16e has a generally dog-bone shape and a generally thicker body than that of applicator 16. Applicator 16e may include a lumen and any of the projections disclosed herein. It also may include a textured outer surface.

The applicator 16f illustrated in FIG. 9 includes a body 30f that is shorter than that of applicator 16. The body 30f may be, for example, between 2 cm and 5 cm. In the illustrated embodiment, applicator 16f has a generally triangular cross-section. In other embodiments, the cross-section of the applicator 16f may be other regular or irregular shapes, such as circular, oval or rectangular. The applicator includes projections 44f that extend into lumen 38f.

The applicator 16g illustrated in FIG. 10 includes an elongated body 30g having a proximal end portion 32g and a distal end portion 34g. Body 30g includes a lumen 38g extending through the proximal and distal end portions 32g, 34g. Body 30g includes slits 46g that extend through body 30g from the proximal end opening 40g to the distal end opening. The slits 46g define projections 44g which extend axially substantially the length of the lumen 38g from the proximal end opening 40g to the distal end opening. In the illustrated embodiment, the applicator 16g has a generally triangular cross-section. In other embodiments, the cross-section of applicator 16g may be other regular or irregular shapes, such as circular, oval or rectangular. Additionally, the body may also include an outer textured surface 31 to aid in grasping the catheter.

It will be understood that any of the projections disclosed herein may be used in combination with any of the applicators disclosed herein or any other suitable applicator for gripping a catheter.

Referring back to FIGS. 1 and 2, during use, the user opens package 12 and removes catheter 14 therefrom by grasping funnel 26 and/or applicator 16. The user may then grasp applicator 16 and slide it proximally along catheter shaft 18. If the user releases their grasp of the applicator 16, the applicator remains in place on shaft 18 due to the contact between projections 44 and shaft 18, as described above. In the illustrated embodiment, at least the intermediate portion 36 of body 30 is elastic. The user pinches or squeezes the intermediate portion 36 which deforms and comes into contact with catheter shaft 18 so that the user may indirectly grasp and handle the catheter shaft through the applicator. The user releases its grasp and moves applicator 16 into a location that allows the user to insert proximal end 20 into the urethra. The user grasps and squeezes the applicator to grip the catheter and begins inserting the catheter into the urethra. After a portion of catheter shaft 18 has been inserted, the user releases their grasp of applicator 16 and moves it distally. The user then again grasps the catheter through the applicator and advances catheter shaft 18 further into the urethra. The user repeats this process until the catheter has reached the bladder and urine drainage begins.

Aspects of the present subject matter described above may be beneficial alone or in combination with one or more other aspects. Without limiting the foregoing description, in accordance with a first aspect, an applicator for gripping a urinary catheter includes a body having a proximal end and a distal end. The body also includes a lumen extending through the proximal and distal end of the body. The lumen has a proximal end opening and a distal end opening and is configured to receive a shaft of a urinary catheter therethrough so that the body is movable distally and proximally along the catheter. The applicator also includes at least one projection disposed within the lumen and contacting the catheter shaft to resist movement of the body along the catheter shaft.

Aspect 2. The applicator of aspect 1 wherein at least a portion of the body is elastically deformable and deforms to contact the catheter shaft for grasping the catheter.

Aspect 3. The applicator of any one of aspects 1 and 2, wherein the at least one projection comprises a plurality of projections.

Aspect 4. The applicator of any one of the preceding aspects wherein the projections comprise petals.

Aspect 5. The applicator of aspect 4 wherein the petals are separated by slits.

Aspect 6. The applicator of aspect 3 wherein the projections have a generally rounded shape.

Aspect 7. The applicator of any one of the preceding aspects wherein the projections are located in the proximal end opening.

Aspect 8. The applicator of any one of the aspects 1-6 wherein the projections are located in the distal end opening.

Aspect 9. The applicator of any one of the preceding aspects wherein the projections are located in both the proximal end opening and the distal end opening.

Aspect 10. The applicator of any one of aspects 1-6 wherein the projections are located distal of the proximal end opening and proximal of the distal end opening.

Aspect 11. The applicator of any of the preceding aspects wherein the body is configured to be releasably attached to a funnel attached to the catheter shaft.

Aspect 12. The applicator of aspect 11 wherein the distal end opening is configured to receive a proximal end of the funnel.

Aspect 13. The applicator of aspect 12 wherein the lumen has a first diameter and the distal opening has a second diameter that is larger than the first diameter.

Aspect 14. The applicator of any one of aspects 1-3 wherein the projections extend substantially the length of the lumen.

Aspect 15. The applicator of any one of the preceding aspects wherein the body includes a gripping surface.

Aspect 16. The applicator of any one of the preceding aspects wherein the projections are in constant contact with the catheter shaft when the catheter shaft is received within the lumen.

Aspect 17. The applicator of any one of the preceding aspects wherein the projections resist free movement of the body along the catheter shaft.

Aspect 18. A urinary catheter assembly, comprising: a catheter package having a cavity; a urinary catheter disposed within the cavity, the catheter including a catheter shaft having a proximal insertion end portion and a distal end portion and a drainage member associated with the distal end portion of the catheter shaft; an applicator for gripping the catheter located within the cavity, the applicator including a body having a proximal end and a distal end; a lumen extending through the proximal and distal ends of the body, the lumen having a proximal end opening and a distal end opening, the shaft of the catheter received within and extending through the lumen, the body being located distal of the proximal insertion end portion of the catheter and being movable proximally and distally along the catheter; and at least one projection disposed within the lumen and in contact with the catheter shaft to resist movement of the body along the catheter shaft.

Aspect 19. The assembly of aspect 18 wherein at least a portion of the body is elastically deformable and deforms to contact the catheter shaft for grasping the catheter.

Aspect 20. The assembly of any one of aspects 18 and 19, wherein the at least one projection comprises a plurality of projections.

Aspect 21. The assembly of any one of aspects 18-20 wherein the projections comprise petals.

Aspect 22. The assembly of aspect 21 wherein the petals are separated by slits.

Aspect 23. The applicator of aspect 20 wherein the projections have a generally rounded shape.

Aspect 24. The assembly of any one of aspects 18-23 wherein the projections are located in the proximal end opening.

Aspect 25. The assembly of any one of aspects 18-23 wherein the projections are located in the distal end opening.

Aspect 26. The assembly of any one of aspects 18-25 wherein the projections are located in both the proximal end opening and the distal end opening.

Aspect 27. The assembly of any one of aspects 18-23 wherein the projections are located distal of the proximal end opening and proximal of the distal end opening.

Aspect 28. The assembly of any one of aspects 18-27 wherein the applicator is configured to be releasably attached to the drainage member.

Aspect 29. The assembly of aspect 28 wherein the distal end opening is configured to receive a proximal end of the funnel.

Aspect 30. The assembly of aspect 28 wherein the lumen has a first diameter and the distal opening has a second diameter that is larger than the first diameter.

Aspect 31. The assembly of any one of aspects 18-20 wherein the projections extend substantially the length of the bore.

Aspect 32. The assembly of any one of aspects 18-31 wherein the body includes a gripping surface.

Aspect 33. The assembly of any one of aspects 18-32 wherein the projections are in constant contact with the catheter shaft when the catheter shaft is received within the lumen.

Aspect 34. The applicator of any one of aspects 18-33 wherein the projections resist free movement of the body along the catheter shaft.

The invention claimed is:

1. A urinary catheter assembly, comprising:
a catheter package having a cavity;
a urinary catheter disposed within the cavity, the catheter including a catheter shaft having a proximal insertion end portion and a distal end portion and a drainage member associated with the distal end portion of the catheter shaft;
an applicator for gripping the catheter located within the cavity, the applicator including
a body having a proximal end and a distal end;
a lumen extending through the proximal and distal ends of the body, the lumen having a proximal end opening and a distal end opening, the shaft of the catheter received within and extending through the lumen, the body being located distal of the proximal insertion end portion of the catheter, wherein a proximal end of the drainage member is located within the distal end of the body to releaseably attach the applicator to the drainage member, and the body being movable proximally and distally along the catheter; and
a plurality of projections disposed within the lumen and in constant contact with the catheter shaft as the body is moved proximally and distally along the catheter and the plurality of projections resisting free movement of the body along the catheter shaft.

2. The assembly of claim 1 wherein at least a portion of the body is elastically deformable and deforms to contact the catheter shaft for grasping the catheter.

3. The assembly of claim 1 wherein the plurality of projections comprise petals.

4. The assembly of claim 3 wherein the petals are separated by slits.

5. The assembly of claim 1 wherein the plurality of projections have a generally rounded shape.

6. The assembly of claim 1 wherein the plurality of projections is located in the proximal end opening.

7. The assembly of claim 1 wherein the plurality of projections is located in the distal end opening.

8. The assembly of claim 1 wherein the plurality of projections is located in both the proximal end opening and the distal end opening.

9. The assembly of claim 1 wherein the plurality of projections is located distal of the proximal end opening and proximal of the distal end opening.

10. The assembly of claim 1 wherein the body is configured to be releasably attached to a drainage member attached to the catheter shaft.

11. The assembly of claim 10 wherein the distal end opening is configured to receive the proximal end of the drainage member.

12. The assembly of claim 11 wherein the lumen has a first diameter and the distal opening has a second diameter that is larger than the first diameter.

13. The assembly of claim 1 wherein the plurality of projections extend substantially the length of the lumen.

14. The assembly of claim 1 wherein the body includes a gripping surface.

15. The assembly of claim 1 wherein the plurality of projections are in constant contact with the catheter shaft when the catheter shaft is received within the lumen.

* * * * *